United States Patent [19]

Tirelli et al.

[11] Patent Number: 5,083,305
[45] Date of Patent: Jan. 21, 1992

[54] RADIATION CONTROL DEVICE WITH VARIABLE ACTIVE SURFACE OF THE TYPE SENSITIVE TO IONIZING RADIATION

[75] Inventors: Marco Tirelli, Villebon sur Yvette; René Romeas, Palaiseau; Yves Gregoire, Paris, all of France

[73] Assignee: General Electric CGR S.A., Issy les Moulineaux, France

[21] Appl. No.: 514,939

[22] Filed: Apr. 26, 1990

[30] Foreign Application Priority Data

Apr. 28, 1989 [FR] France .................. 89 05665

[51] Int. Cl.⁵ .............................................. A61B 6/04
[52] U.S. Cl. .................................... 378/37; 378/145
[58] Field of Search ........................ 378/145, 37

[56] References Cited

U.S. PATENT DOCUMENTS

| | | |
|---|---|---|
| 3,824,397 | 7/1974 | Bauer et al. |
| 3,991,316 | 11/1976 | Schmidt et al. ............ 378/37 |
| 4,707,846 | 11/1987 | Sportelli ..................... 378/145 |
| 4,825,455 | 4/1989 | Bauer ......................... 378/37 |
| 4,943,991 | 7/1990 | Mosby ........................ 378/37 |
| 4,947,417 | 8/1990 | Hartwell ..................... 378/37 |

FOREIGN PATENT DOCUMENTS 0158838 10/1985 European Pat. Off.

OTHER PUBLICATIONS

Radiology, 125, 1978, U.S.A., pp. 517-523, Muntz, et al., "Preliminary Studies Using Electron Radiography for Mammography".

Primary Examiner—Craig E. Church
Attorney, Agent, or Firm—Oblon, Spivak, McClelland, Maier & Neustadt

[57] ABSTRACT

Disclosed is a radiology system of the mammograph type in which there is provision for a radiation controller. The invention lies in the fact that the input aperture of the detector is masked by a belt that absorbs the X-radiation except at zones, the variable dimensions of which are designed to get adapted to the different shapes of breasts. The belt is driven by a motor 24 and stops at the practitioner's command so that the appropriate zone is in correspondence with the input aperture of the detector 22.

5 Claims, 3 Drawing Sheets

RADIATION CONTROL DEVICE WITH VARIABLE ACTIVE SURFACE OF THE TYPE SENSITIVE TO IONIZING RADIATION

BACKGROUND OF THE INVENTION

1. Field of the Invention

The invention concerns radiology systems, such as mammographs and, more particularly in such systems, a device that can be used to control the dose of radiation received by a person during examination as well as the exposure time so as to obtain an image with the optimum contrast for a minimum dose of radiation.

2. Description of the Prior Art

As shown in FIG. 1, radiology systems of the mammography type comprise an X-radiation source 10, borne by a bracket II placed at the top of a vertical plate 12. This plate has an assembly 13 on which the breast 16 to be examined rests by means of a horizontal shelf 15. A pad 17, transparent to X-radiation and vertically movable on the plate 12, is used to compress the breast.

To get adapted to the patient's size, the plate 12 is mounted on a vertical column 9 resting on the ground, and moves vertically on said column by means of an appropriate mechanical device.

On its upper part and beneath the shelf 15, the assembly 13 has a tunnel in which there is housed a cartridge 18 formed by a black box enclosing a film 14 sensitive to the direct X-radiation or to a photon radiation emitted by a screen (not shown) receiving the X-radiation. It is on this film 14 that the latent image of the breast is formed after an appropriate exposure time. The development of the film gives an X-ray photograph.

For the photograph to be useful for the purposes of diagnosis, all the points that form the image of the examined object should have sufficient contrast with one another. In particular, the blackening of the film should be right and "standardized" for a very wide range of opacity of the object. To this effect, the blackening may be controlled by a radiation control device which is placed beneath the cartridge 18 in the lower part 8 of the assembly 13. This control device, also called an exposer, is formed by an X-radiation detector that delivers an electrical signal proportionate to the flow-rate of the dose of X-radiation that passes through the sensitive film. This electrical signal, which expresses the intensity of the X-radiation, is integrated during the exposure time and the signal resulting from this integration is compared at each instant with a pre-determined threshold signal which is a function of the characteristics of the sensitive film. As soon as the integrated signal reaches this threshold, the signal indicating equality controls the source to be turned off, and this ends the exposure time.

One of the advantages of this radiation control device is that, for a wide-ranging variation in the X-radiation flow-rates leading to differences in exposure, it makes it possible, firstly, to obtain an exposure of sensitive film corresponding to an optimum contrast and, secondly, to have more efficient control over the mean dose received by the patient, this dose being a major factor in the assessment of carcinogenic risk.

In a radiation control device, it is important that the detector should receive only the radiation that has gone through the breast, for the reception of an unattenuated radiation would falsify the measurement. Hence, the receiving surface of a detector such as this is limited by the size of the smallest breast to be examined. A limitation of this kind would considerably restrict the advantages that might be drawn from this device, and would constitute a factor of error in certain circumstances, for the zone of the object corresponding to the size of the detector may be different from the one examined. For, the position of the detector is generally fixed whereas the zone to be examined may have a position that is variable with respect to that of the detector and, therefore, there is not the overlapping desired for an optimum measurement.

This limitation is even more pronounced in mammography for there is great disparity among the individuals observed and, for one and the same individual, there is a disparity depending on the instant at which the examination is performed in relation to the hormone cycle. In the first category, there are anatomical differences such as the size of the breast and the local composition of the tissues. In the second category, there is the composition and distribution of the tissues as a function of the hormone cycle, age, weight and somatic development. In addition, there is the density and distribution of the structures to be displayed, whether they are pathological or not, whether they are massive or whether they are micro-calcifications, the positions of which are not known to the practitioner.

In short, with a small-sized detector having a fixed position, the measuring signal does not represent the breast in its entirety and may lead to under-exposed photographs when the detector is beneath an adipose part of the breast or over-exposed photographs when the detector is beneath a fibrous part or beneath a region of pathological opacity.

Owing to the above-mentioned inadequacies, it will be difficult for the practitioner to use the photographs obtained to make a diagnosis or a preventive check-up with a high degree of certainty. He will therefore be led to repeat the examination so that the advantages of the use of a detector, namely speed, greater contrast, reduction in the dose of radiation and reduction in kinematic blur, are jeopardized.

These drawbacks are partially attenuated in systems where the entire detector assembly can be shifted in its plane beneath the breast. However, there is a limit to the greatest possible dimension of the detector and, consequently, this detector is badly optimized with respect to the different sizes of breast encountered. In this case, the signal resulting from the integration is an approximation of the optimum signal: it is therefore experience that must guide the practitioner in his choice of the position of the detector.

Besides, it is hardly possible to predict the position at which the regions of opacity will be located on the photograph, whence the difficulty of choosing the position of the cell in the first photograph.

SUMMARY OF THE INVENTION

The aim of the present invention, therefore, is the making of a radiation control device that can be adapted to different sizes of the object to be X-rayed. To this effect, the invention proposes, firstly, the enlargement of the dimensions of the detector up to, possibly, the dimensions of the sensitive film and, secondly, the use of masks of different dimensions that are placed between the cartridge and the detector or between the film sensitive to X-radiation and the detector.

The invention pertains to a device for the control of radiation in a radiology system that comprises at least one source of X-radiation emitting a beam that irradiates an object to be observed, a sensitive film placed beneath the object on which the latent image of said object is formed and a detector of X-radiation that has gone through the object to be observed and the sensitive film, said detector giving an electrical signal used to control the time of exposure of the object, said device further comprising at least one mask with opacity appropriate to the energy of the X-radiation, placed between the sensitive film and the detector, said mask having at least one zone that does not absorb the X-radiation, the shape and the area of the non-absorbent zone being adapted to the dimensions of the object to be observed and/or to the type of examination that is performed.

In a simplified embodiment, the mask is supported by a frame which is positioned movably before the detector. In a more elaborate embodiment, the mask is supported by a belt associated with a mechanism for the shifting of said belt so as to place said zone that does not absorb X-radiation in an optimal position with respect to the object to be observed.

Furthermore, this belt has several zones that do not absorb X-radiation, that are preferably arranged successively in the direction in which the belt is shifted, the dimensions and shape of these zones being different from one zone to the next one so as to get adapted to the dimensions and shape of the object ,as well as to the type of examination performed. The X-radiation detector may be of the type comprising an ionization chamber or of the semi-conductor type.

BRIEF DESCRIPTION OF THE DRAWINGS

Other characteristics and advantages of the present invention will appear from the following description of a particular embodiment, said description being made with reference to the appended drawings, wherein.

DESCRIPTION OF A PREFERRED EMBODIMENT

The invention shall be described in its application to a mammograph, but it can be implemented in other systems of radiology where use is made of a radiation controller of the type that converts an X-radiation into an electric signal. In order to adapt the radiation control more efficiently to the zone to be examined, irrespectively of the size of the breast, the invention proposes the modification of the surface of the active zone of the radiation converter through the positioning, above this radiation detector, of a mask absorbing said radiation, which has windows that are non-absorbent with respect to said radiation, with dimensions and shapes that vary as a function of those of the breast to be examined.

Figure 3:
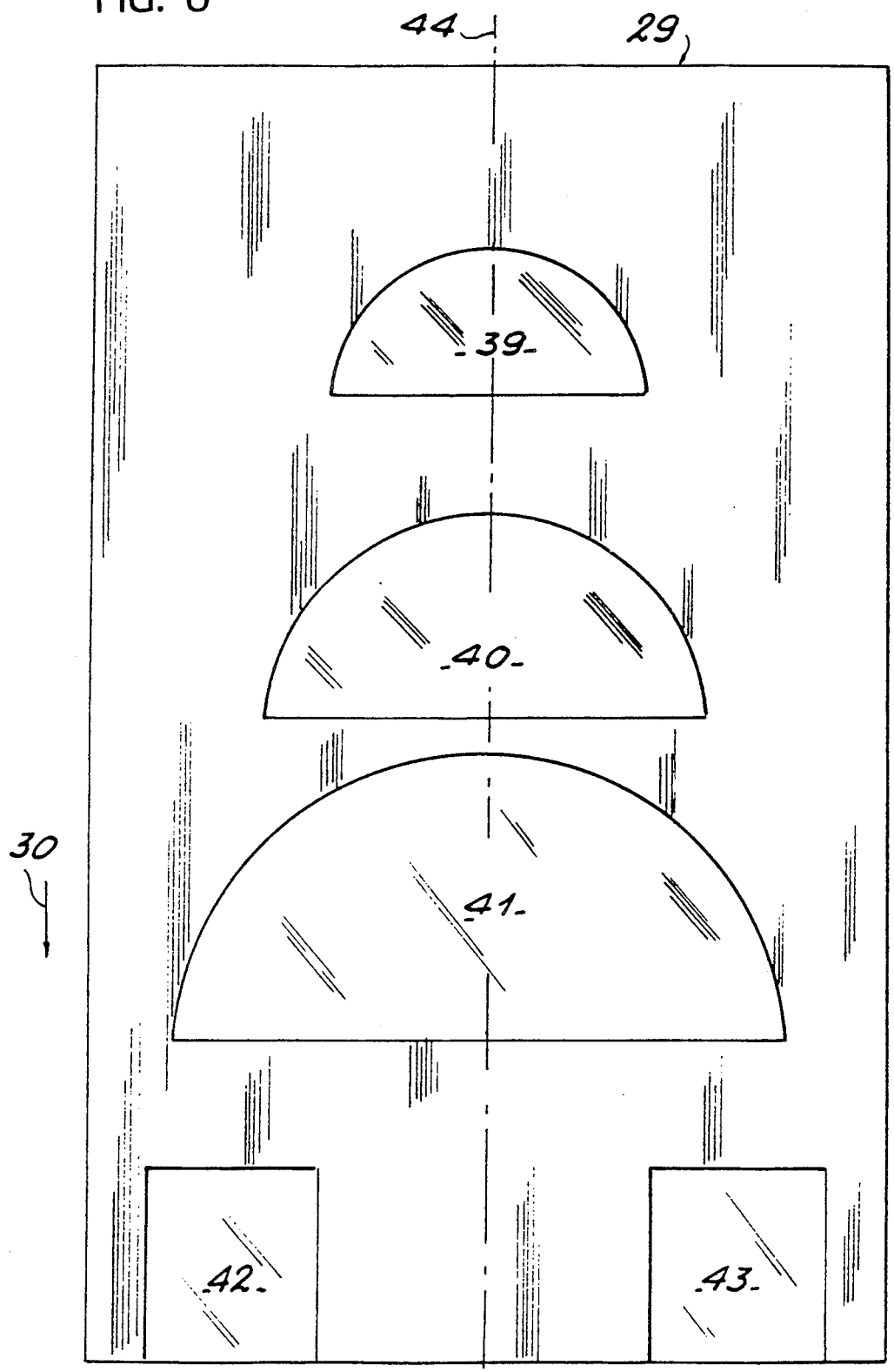
FIG. 3 is an spread-out view of the belt showing the different zones that are non-absorbent with respect to X-radiation.
Figure 4:
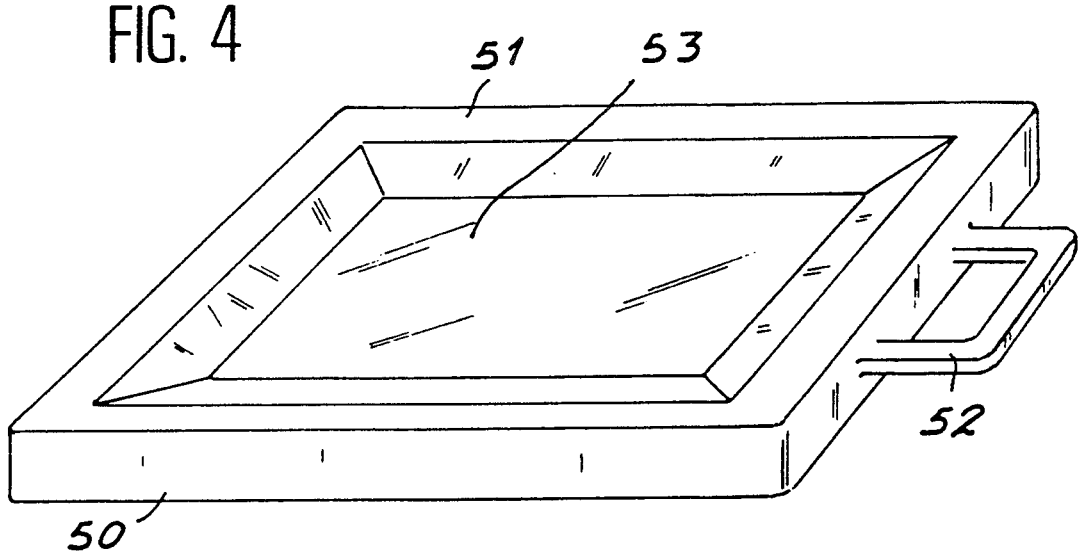
FIG. 4 is a perspective view of a drawer device enabling the masks of the detector to be changed by hand as a function of the anatomical dimensions of the breast.
Figure 5A:
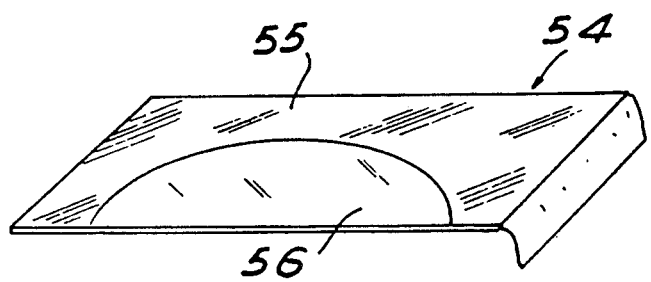
FIGS. 5a and 5b show the respective shapes and sizes of two manually positioned masks.
Figure 5B:
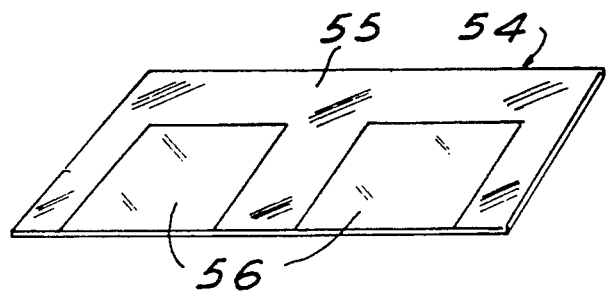

To achieve this kind of interposition of a mask, the invention proposes an automatic device (FIGS. 2 and 3) and a manual device (FIGS. 4 and 5). The automatic device is positioned in the lower part 8 of the assembly 13 beneath the cartridge 18. This cartridge 18 has, in a known way, a sensitive film 20 inside a case or inside a black box formed by the cartridge and a zone 21 non-absorbent with respect to X-radiation, located in the lower wall of the cartridge 18 and in the vicinity of the external edge 32 of the part closest to the patient. The radiation detector 22 is formed, for example, by an ionization chamber or by a semi-conductor device which gives an electrical signal to a conductor 28 when it receives an X-radiation going through the zone 21.

The detector 22 is fixed beneath the window 21 to a frame 31, formed essentially by the lower part 8 of the assembly 13. On top of the detector 22, there is placed a belt 23 which is supported and driven in motion in the direction of the arrow 30 by a driving motor 24 and supporting rollers 25, 26 and 27. The belt 29 is shaped as a loop and absorbs X-radiation throughout its surface, except for the zones 39, 40, 41, 42 and 43 (FIG. 3). The zones 39, 40 and 41 have a general shape of a semi-circle, the diameter of which varies from one zone to the next, the zone 39 with the smallest diameter being intended, for example, for the examination of small breasts, the zone 40 for the examination of medium-sized breasts and the zone 41 for the examination of big breasts. Finally, the zones 42 and 43, which are rectangular and are positioned symmetrically on either side of the longitudinal axis of symmetry 44 of the belt, are used during a stereotaxic examination to obtain two views on the same film.

Depending on the length of the belt 29, it is possible to create a number of windows, such as 39, 40 and 41, that is greater than three in order to cover differences in breast sizes more efficiently. Furthermore, these zones may have shapes other than that of a semi-circle. Clearly, the maximum dimensions of the window 41 or of the rectangle encompassing the windows 42 and 43 are those of the input face of the detector 22.

During an examination, the choice of the window that is adapted to the breast observed is done by the practitioner, and the electrical control circuit of the driving motor 24 is designed to place the chosen window before the input aperture of the detector 22, the base of the semi-circle being located towards the external edge 32 of the assembly 13, as close as possible to the patient.

Figure 2:
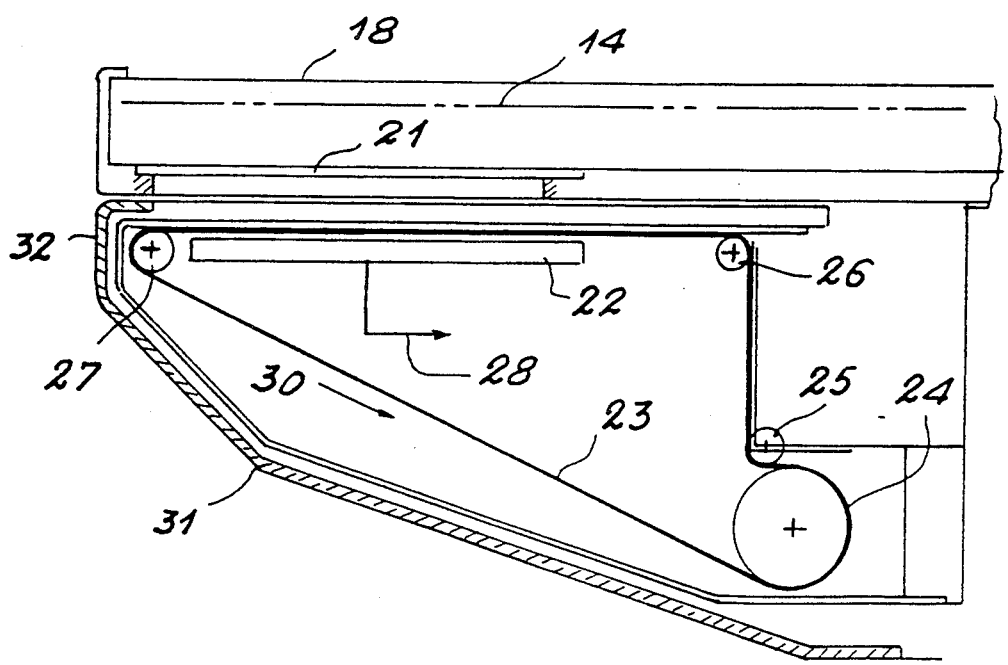
FIG. 2 shows a schematic vertical section of a particular embodiment of an automatic mask-changing device according to the invention.

FIGS. 4 and 5 show embodiments of a manual device. It includes a drawer 50 (FIG. 4) which is positioned between the cartridge 18 or the film in a case and the detector 22 (FIG. 2). Preferably, this drawer is placed parallel to the lower wall of the cartridge 18, beneath the zone 21, or directly beneath the case that contains the film sensitive to X-radiation. The drawer 50 consists of a frame 51 provided with an operating handle 52. The central zone 53 absorbs no X-radiation and its rim acts as a support to a mask 54 (FIG. 5) formed by an external zone 55 opaque to X-radiation and a central zone 56 having a window transparent to X-radiation. There is provision for using several masks wherein the dimensions of each window vary from one mask to another, each window corresponding, for example, to a window of the belt shown in FIG. 3.

Figure 1:
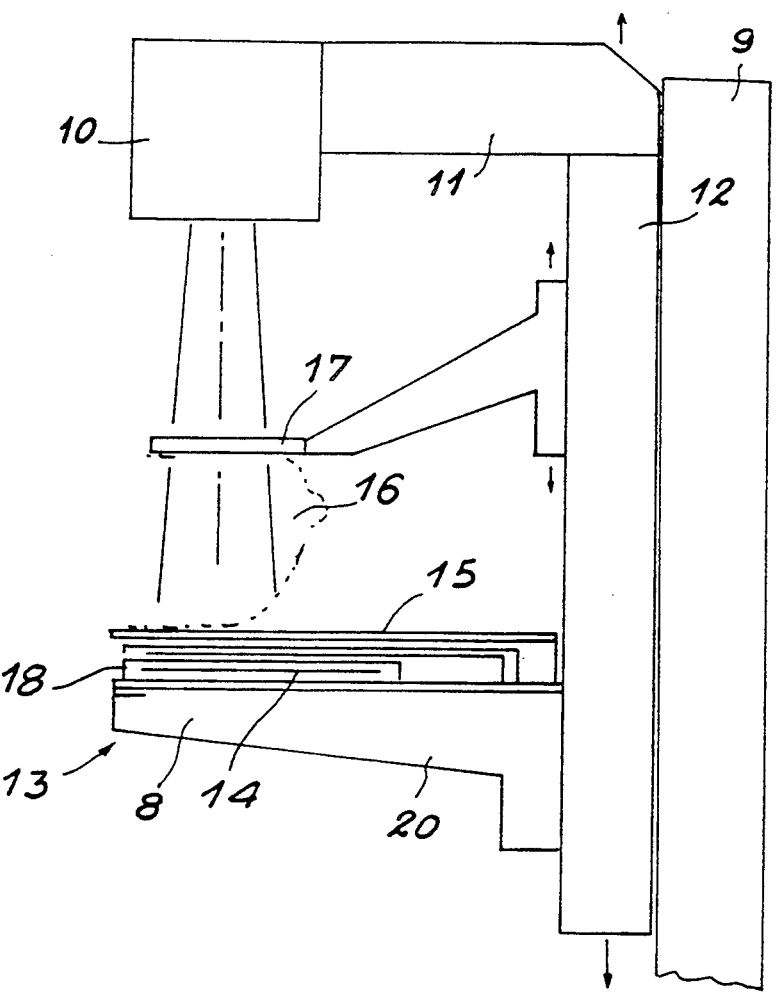
FIG. 1 shows a schematic vertical section of a mammograph in a plane passing through the source of the X-radiation.

In the case of FIGS. 4 and 5, the drawer 50 is designed to be fitted into the assembly 13, preferably by one of the two lateral sides parallel to the plane of the FIG. 1. It is also possible to fit the drawer in by the external edge 32 but, in this case, it is necessary to do so before the positioning of the patient.

In the case of the automatic device of FIGS. 2 and 3, the direction of the shift of the belt 29 has been designed to take place in the direction of the arrow 30. It is clear that the invention can also be implemented by means of a belt that would move in a direction perpendicular to the plane of FIG. 1. In this case, the windows 39 to 43 would have to be rotated by 90° so that the base of the semi-circle is parallel to the direction of the shift.

The belt 29 may be made, for example, by means of a flexible material which is coated with a material with an opacity appropriate to the range of X-radiation used, except at the non-absorbent zones 39 to 43. This material opaque to X-radiation has to be flexible enough not to excessively reduce the flexibility of the belt 29, and so that it has no cracks, notably after lengthy use, for these cracks would falsify the measurements of the detector 22.

What is claimed is:

1. A device for the control of x-ray radiation exposure of a film sensitive to x-rays in a radiology system that comprises at least one source of X-radiation emitting a beam that irradiates an object to be examined, said film sensitive to x-rays placed beneath said object on which the latent image of the object is formed, and a detector of the X-radiation that has gone through the object to be examined, of the type having an ionization chamber, said chamber giving an electrical signal used to control the time of exposure of the object, said device further comprising a mask opaque to the X-radiation which is placed above the ionization chamber and below said object to be examined, said mask having at least one zone that is transparent to the X-radiation, the shape and the area of the transparent zone being adapted to the dimensions of the object to be observed and to the type of examination that is performed, wherein the mask is supported by a belt associated with a mechanism for the shifting of said belt so as to place said transparent zone in an optimal position with respect to said object.

2. A control device according to claim 1, wherein the mask is supported by a frame, said frame positioned movably above the ionization chamber.

3. A control device according to claim 1, wherein said mask has a plurality of zones transparent to x-rays.

4. A control device according to claim 1, further comprising:
a pad which is transparent to x-rays below the source of X-radiation, and above said object to be examined; and
means to move said pad in the vertical direction and to press said pad down upon said object to be examined.

5. A control device according to claim 1, wherein said belt has several zones transparent to X-radiation that are arranged successively in the direction in which the belt is shifted, the dimensions and shape of these zones being different from one zone to the next one so as to get adapted to the dimensions and shape of the object as well as to the type of examination performed.

* * * * *